(12) United States Patent
Jayalekshmy et al.

(10) Patent No.: US 7,396,554 B2
(45) Date of Patent: Jul. 8, 2008

(54) ANTIOXIDANT SESAME EXTRACT

(75) Inventors: Ananthasankaran Jayalekshmy, Kerla (IN); Chami Arumughan, Kerla (IN); Kizhiyedathu Polachira Suja, Kerla (IN)

(73) Assignee: Council of Scientific & Industrial Research, Kerla (IN)

( * ) Notice: Subject to any disclaimer, the term of this patent is extended or adjusted under 35 U.S.C. 154(b) by 675 days.

(21) Appl. No.: 10/642,364

(22) Filed: Aug. 15, 2003

(65) Prior Publication Data

US 2004/0121058 A1 Jun. 24, 2004

Related U.S. Application Data

(60) Provisional application No. 60/404,004, filed on Aug. 16, 2002.

(51) Int. Cl.
*A23L 1/36* (2006.01)

(52) U.S. Cl. .......................... 426/629; 426/451

(58) Field of Classification Search ................ 426/541, 426/629
See application file for complete search history.

(56) References Cited

U.S. PATENT DOCUMENTS

| | | | | |
|---|---|---|---|---|
| 2,159,465 | A | | 5/1939 | Williams .................... 192/6 |
| 2,786,063 | A | * | 3/1957 | Purdy et al. ................ 549/435 |
| 2,837,534 | A | * | 6/1958 | Tracy ........................ 549/435 |
| 4,442,092 | A | * | 4/1984 | McBrayer ................... 424/773 |
| 4,649,206 | A | * | 3/1987 | Namiki et al. .............. 549/435 |
| 5,017,397 | A | | 5/1991 | Nguyen et al. .............. 426/542 |
| 5,043,100 | A | | 8/1991 | Chang et al. ................ 252/398 |
| 5,132,294 | A | | 7/1992 | Mimura et al. .............. 514/53 |
| 5,527,552 | A | | 6/1996 | Todd, Jr. .................... 426/541 |
| 5,606,035 | A | * | 2/1997 | Kawakishi et al. ........... 536/4.1 |
| 5,811,313 | A | * | 9/1998 | Barr .......................... 436/161 |
| 7,029,717 | B1 | * | 4/2006 | Ojima et al. ................ 426/548 |

FOREIGN PATENT DOCUMENTS

| | | | |
|---|---|---|---|
| JP | 59-157173 | * | 9/1984 |
| JP | 62-172086 | * | 7/1987 |
| JP | 62-238287 | * | 10/1987 |
| JP | 63-152965 | * | 6/1988 |
| JP | 1-202278 | * | 8/1989 |
| JP | 6-116282 | * | 4/1994 |
| JP | 10-52219 | * | 2/1998 |
| JP | 2001-299289 | * | 10/2001 |

OTHER PUBLICATIONS

Shimizu et al. Sesamin is a Potent and Specific Inhibitor of Desaturase in Polyunsaturated Fatty Acid Biosynthesis. Lipids, vol. 26, No. 7. 1991.*

Chavali et al. Increased Survival After Cecal Ligation and Puncture in Mice consuming Diets Enriched with Sesame Seed Oil. Critical Care Medicine. vol. 29(1). Jan. 2001.*

(Continued)

*Primary Examiner*—Anthony Weier
(74) *Attorney, Agent, or Firm*—Ladas & Parry LLP

(57) ABSTRACT

An antioxidant extract from sesame seed/cake containing sesamol and other compounds is prepared by employing selective extraction techniques and purification methods and that which can be effectively utilised as a substitute for synthetic antioxidants for the protection of vegetable oils, foods, cosmetic/pharmaceutical preparations etc.

6 Claims, 12 Drawing Sheets

Peroxide value(milli equiv $O_2$/kg) of soybean oil stored at 60°C

OTHER PUBLICATIONS

ESP@Cenet Database Abstract. JP 3231996. Published Oct. 1991. Inventor: Yasuhiro et al.*

Fennema, O., *Principles of Food Science: Part I: Food Chemistry*, University of Wisconsin-Madison, Wisconsin, Markel & Dekker Inc., pp. 166-169 (1976).

Hui, Y.H., *Bailey's Industrial Oil and Fat Products*, Fifth Edition, vol. 2, pp. 466-471, 474-475 (1996).

Katasuzaki, H., et al., "Sesaminol Glucosides In Sesame Seeds," *Phytochemistry*, vol. 35, No. 3, pp. 773-776 (1994).

Katsuzaki, H., et al., "Structure of Novel Antioxidative Lignan Glucosides Isolated From Sesame Seed," *Biosci.Biotech.Biochem*, Department of Food Science and Technology, Nagoya University, Japan, vol. 56, No. 12, pp. 2087-2088 (Jul. 24, 1992).

Nagata, M., et al., "Solution of Lignan Analogues to Antioxidative Activity of Used Unroasted Seasame Seed Oil," *JAOCS*, vol. 63., No. 8, pp. 1027-1030 (Aug. 1986).

Namiki, M., "The Chemistry and Physiological Functions of Sesame," *Food Review: International*, vol. 11, No. 2, pp. 281, 286-288, 291-296, 311-320 (1995).

Shahidi, F., *Natural Antioxidants: Chemistry, Health Effects, and Applications,* Department of Biochemistry, Memorial University of Newfoundland, St. John's, Newfoundland, Canada, AOCS Press, pp. Preface, 64-67 (1997).

Shyu, Y.S., et al., "Antioxidative Activity of the Crude Extract of Lignan Glycosides From Unroasted Burma Black Sesame Meal," *Food Research International*, pp. 357-365 (2002).

Tian, L.L., et al., "Antioxidant Activity of Oat Extract in Soybean and Cottonseed Oils," *JAOCS*, vol. 71, No. 10., pp. 1079-1086 (Oct. 1994).

Yoshida, Y., et al., "Antioxidative Effects of Sesamol and Tocopherois at Various Concentrations In Oils During Microwave Heating," *Journal of the Science of Food and Agriculture*, pp. 220-226 (1999).

* cited by examiner

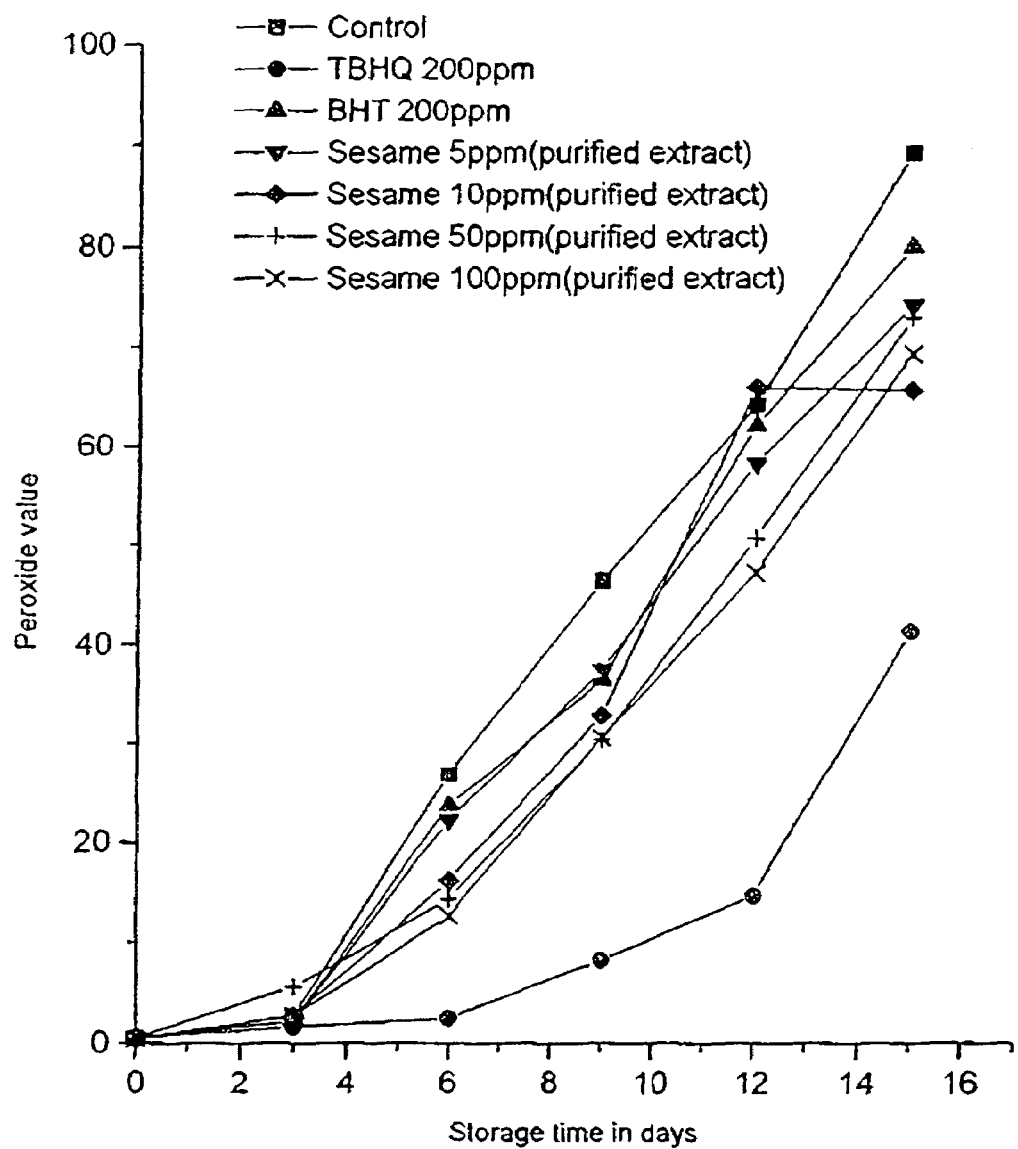
Fig. 1. Peroxide value (milli equiv $O_2$/kg) of soybean oil stored at $60^0C$

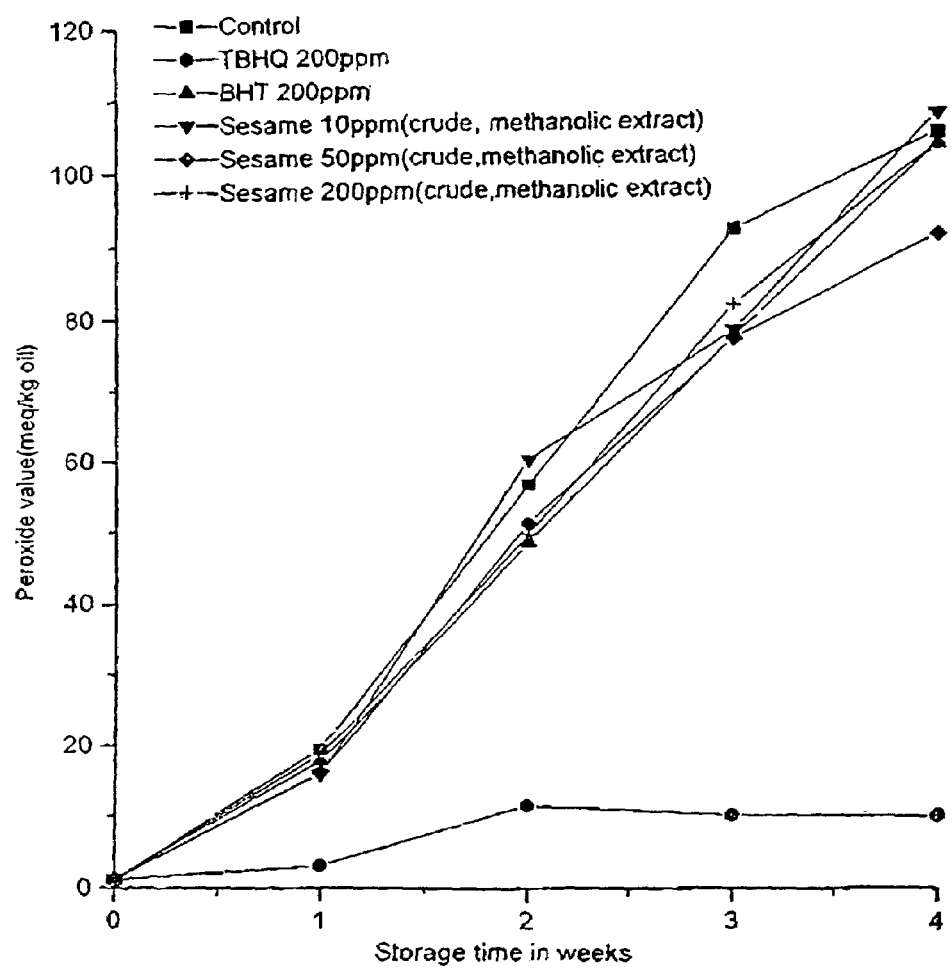
Fig. 1a. Peroxide value (milliequiv. $O_2$/Kg) of Soybean oil stored at 60°C

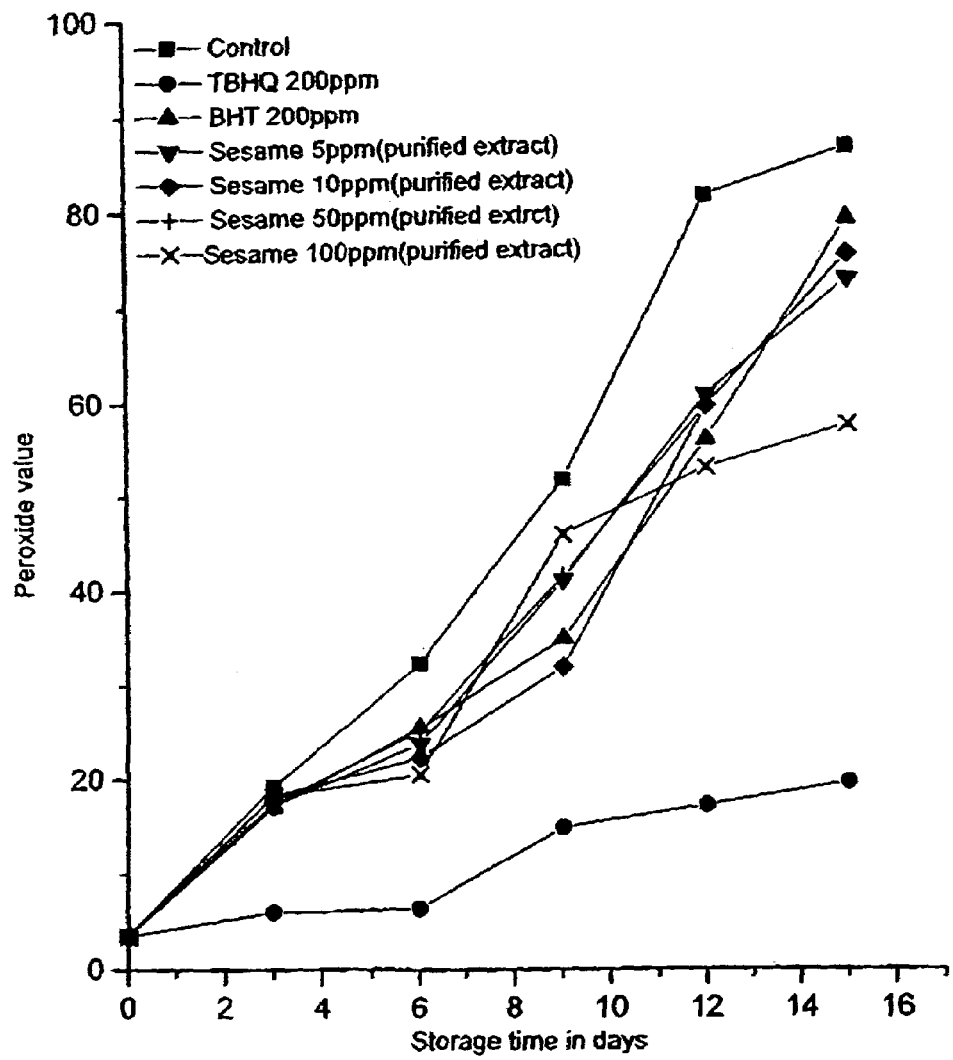
Fig.2. Peroxide value (milli equiv.$O_2$/Kg) of safflower oil stored at $60°C$

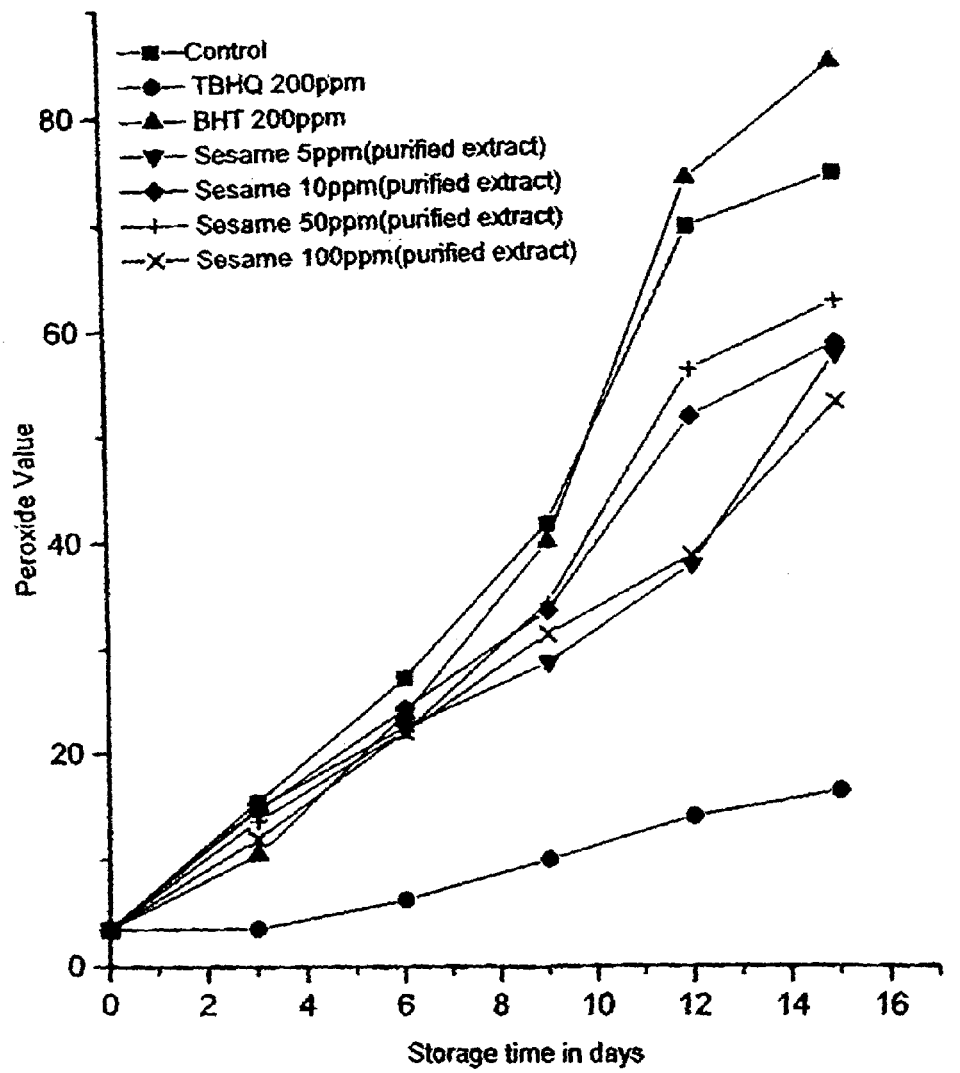
Fig.3.Peroxide Value(milli equiv.$O_2$/Kg) of Sunflower oil stored at 60 °C

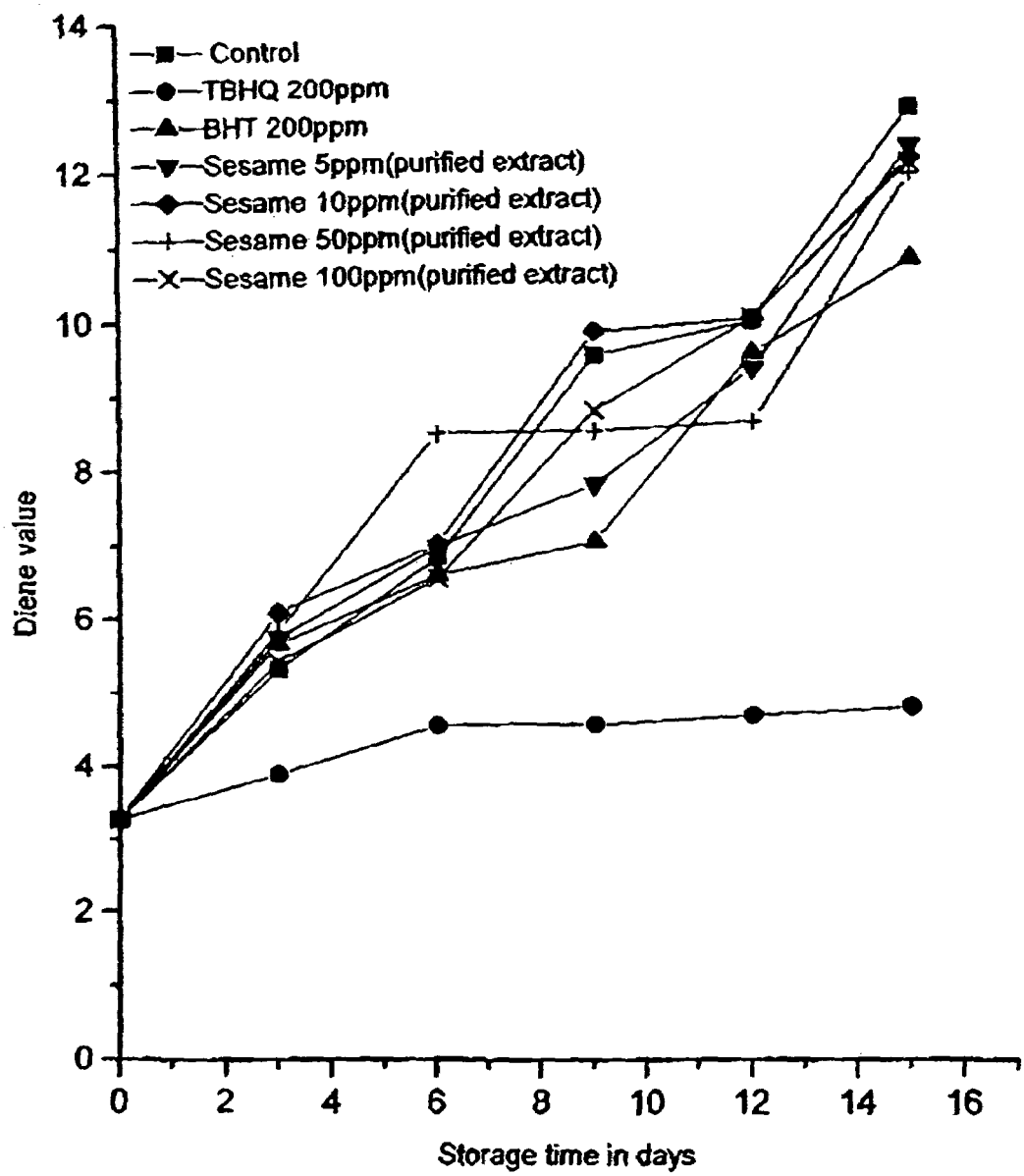
Fig.4. Diene Value of Safflower oil stored at 60°C

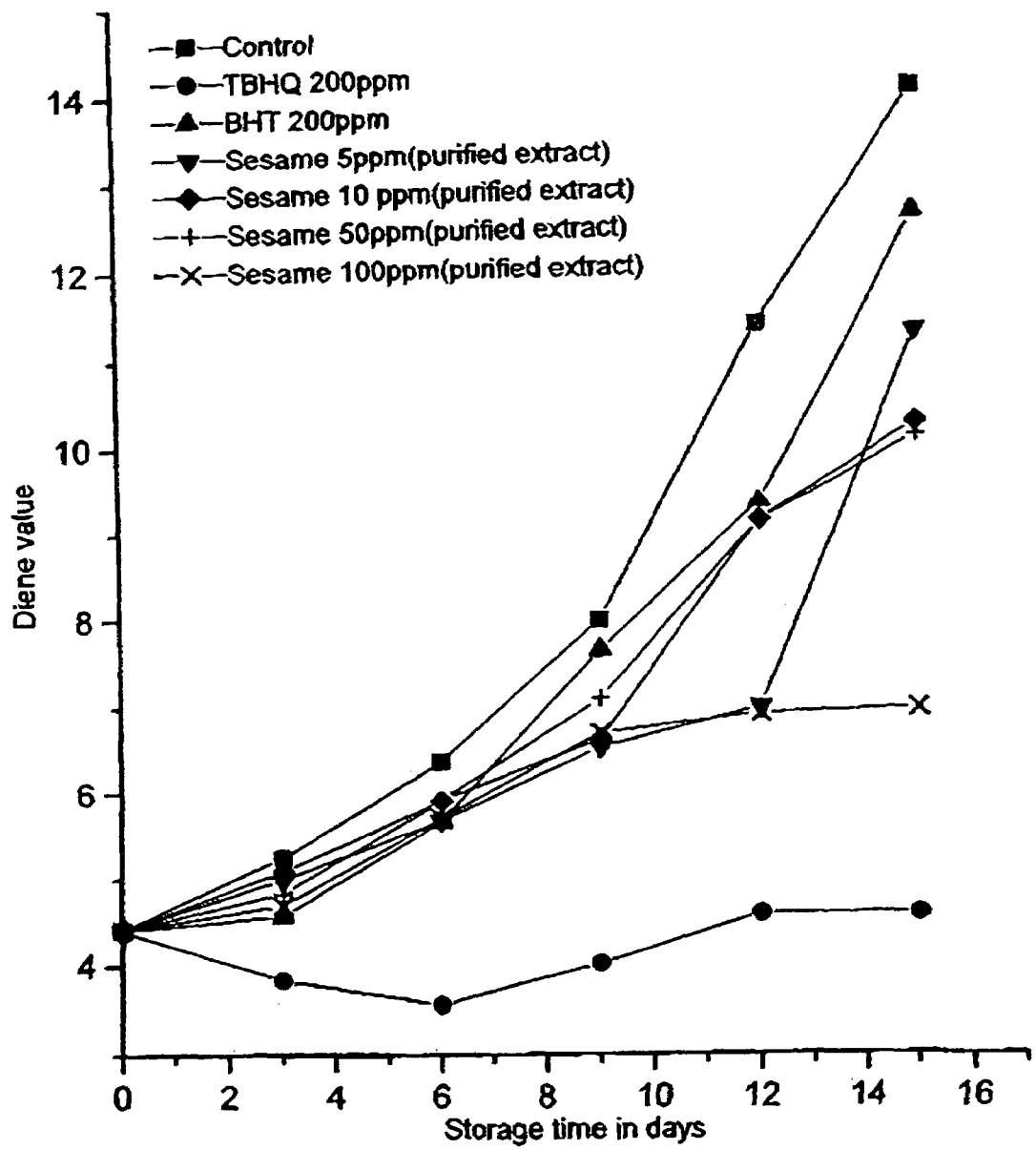
Fig.5.Diene Value of Sunflower oil stored at 60° C

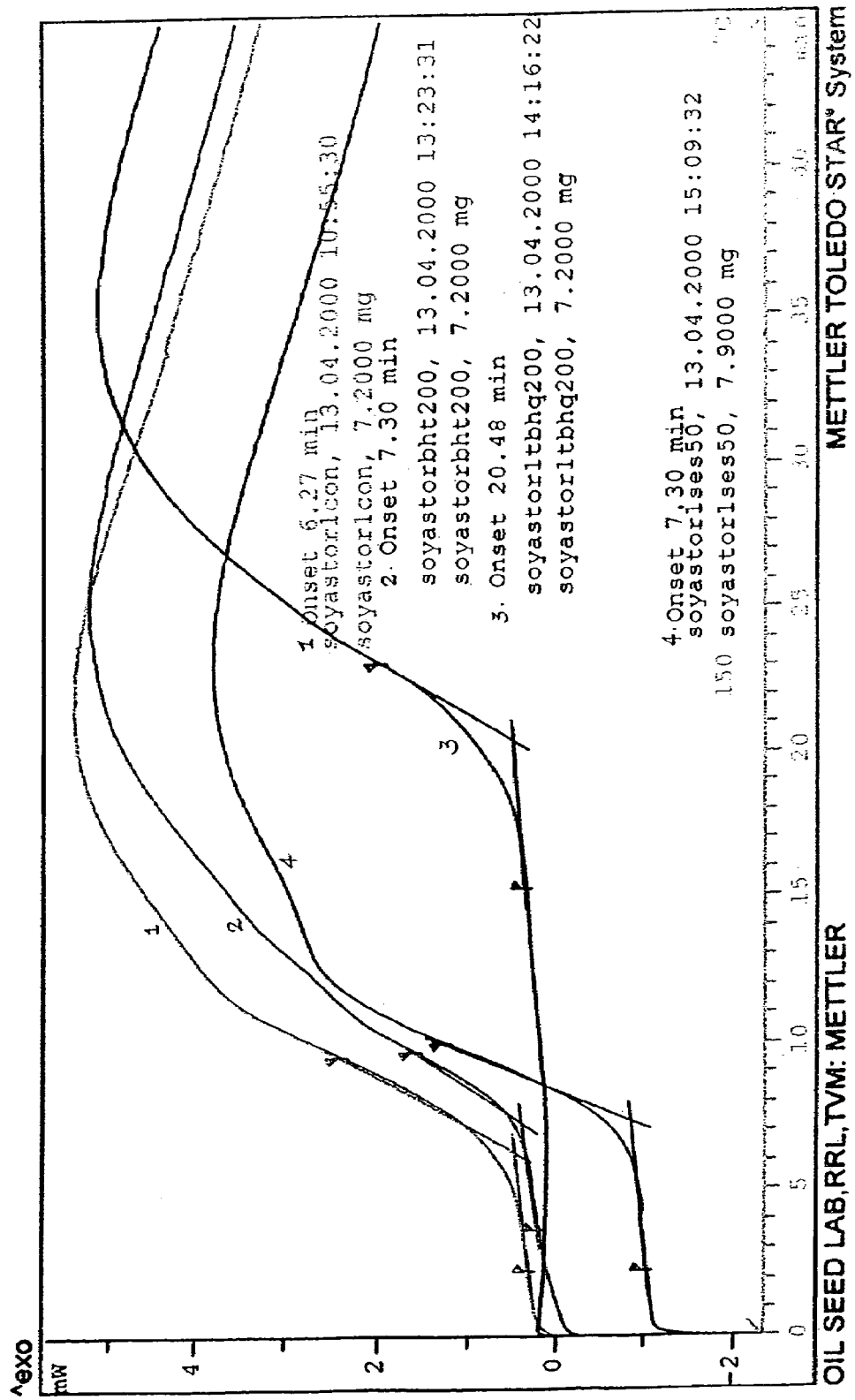
Fig. 6. DSC profile of oxidative stability of soybean oil containing synthetic and sesame antioxidants at different concentrations (in ppm).

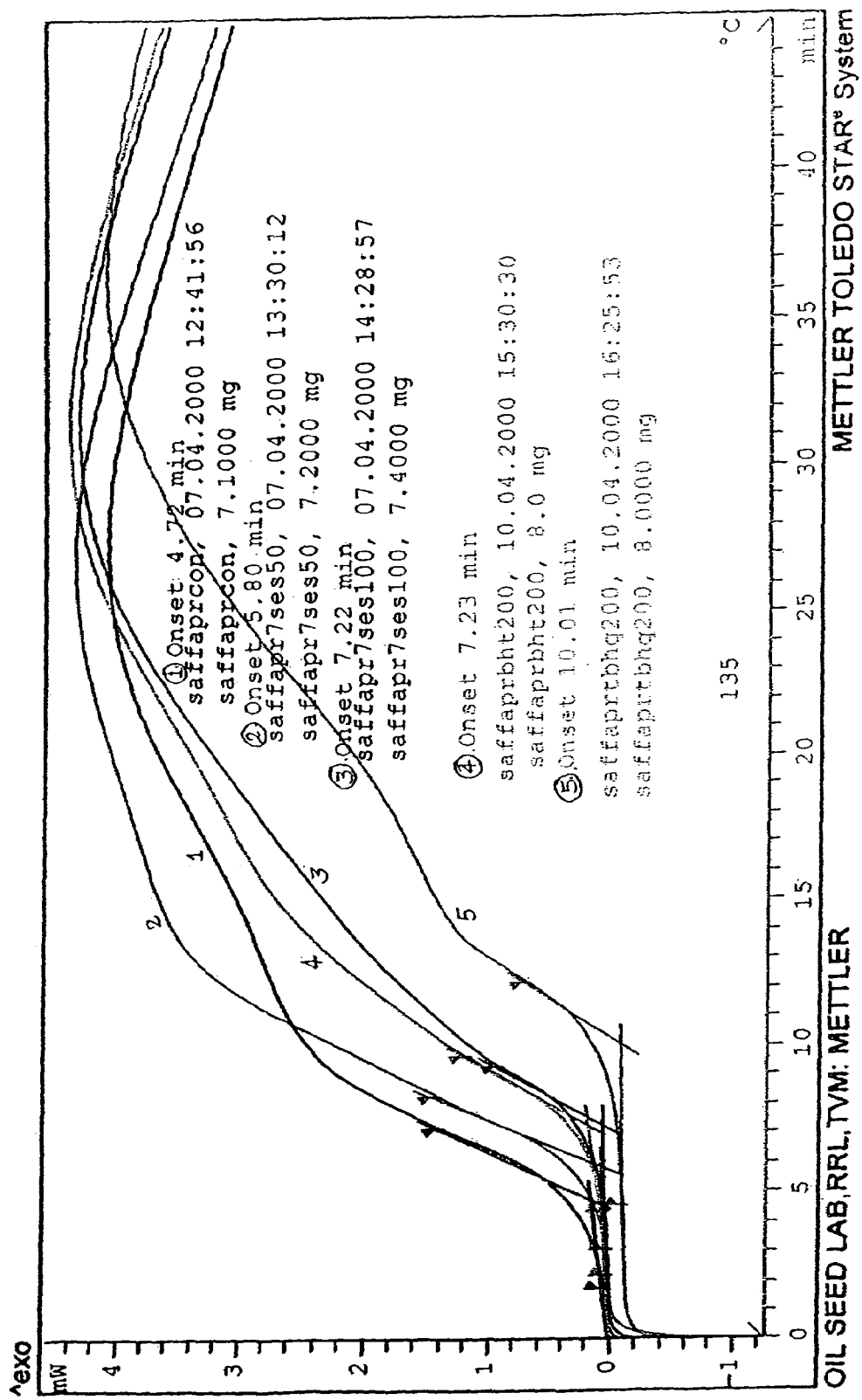
Fig. 7. DSC profile of oxidative stability of safflower oil containing synthetic and sesame antioxidants at different concentrations (in ppm).

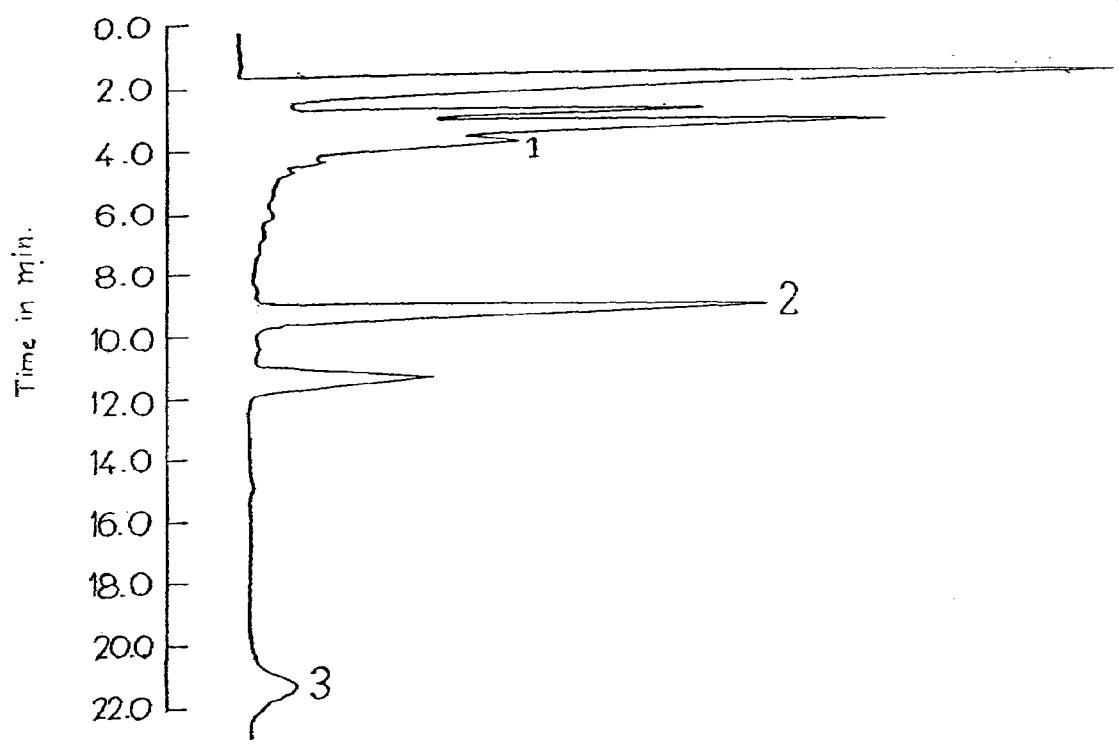
Fig.8: HPLC Profile of Sesame extract
(1) Sesamol (2) Sesamin (3) Sesamolin

```
C-R7A CHROMATOPAC CH=1  REPORT No.=4   DATA=2:MABEL.C32 00.08 08  12:57:14
```

CALCULATION REPORT

| CH | PKNO | TIME | AREA | HEIGHT | MK | IDNO | CONO | NAME |
|---|---|---|---|---|---|---|---|---|
| 1 | 1 | 2.162 | 11994 | 1299 |  |  | 1.7548 |  |
|  | 2 | 2.311 | 12797 | 767 | V |  | 1.8724 |  |
|  | 3 | 3.362 | 61832 | 4088 | V |  | 9.0466 |  |
|  | 4 | 3.636 | 33442 | 2503 | V |  | 4.8929 |  |
|  | 5 | 3.919 | 55292 | 3115 | V |  | 8.0898 |  |
|  | 6 | 4.391 | 29323 | 1391 | V |  | 4.2902 |  |
|  | 7 | 4.787 | 11002 | 666 | V |  | 1.6098 |  |
|  | 8 | 5.144 | 9528 | 599 | V |  | 1.394 |  |
|  | 9 | 6.705 | 1186 | 74 |  |  | 0.1736 |  |
|  | 10 | 7.742 | 8433 | 436 |  |  | 1.2338 |  |
|  | 11 | 8.781 | 373966 | 20057 |  |  | 54.7152 |  |
|  | 12 | 9.667 | 26034 | 1090 | V |  | 3.8091 |  |
|  | 14 | 10.904 | 5042 | 174 | V |  | 0.7377 |  |
|  | 15 | 11.793 | 10121 | 309 | V |  | 1.4809 |  |
|  | 16 | 21.718 | 33486 | 555 |  |  | 4.8993 |  |
|  |  | TOTAL | 683476 | 37124 |  |  | 100 |  |

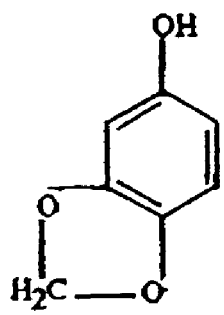
Structure 1. Sesamol
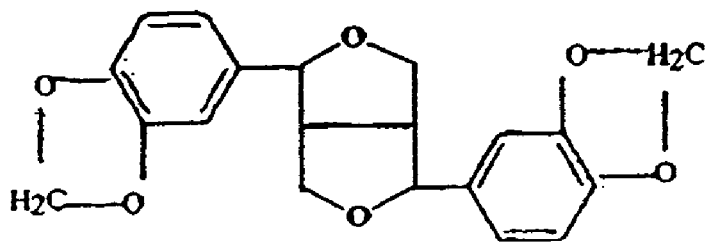
Structure 2. Sesamin
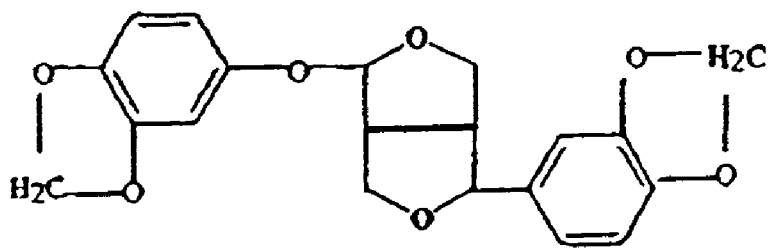
Structure 3. Sesamolin
Fig. 11

ANTIOXIDANT SESAME EXTRACT

This application makes a right of priority claim under 35 U.S.C. § 119(e) for the benefit of the filing date of U.S. Application No. 60/404,004, which was filed on Aug. 16, 2002. The entire contents of U.S. Application No. 60/404,004 are hereby incorporated herein in their entirety by this reference.

This invention relates to an antioxidant extract from sesame seeds/cakes and a process for the extraction of antioxidant substances from sesame seed/cake. The antioxidant concentrate is prepared from commercially available sesame seed/oilcake (starting material). The antioxidant extract is prepared through selective extraction steps employing organic and or aqueous solvents. The final concentrate obtained is dissolved in a suitable permitted, non-ionic lipid dispersible carrier. The antioxidant so obtained is effective in protecting common vegetable oils/emulsions/lipid systems in foods, cosmetics, pharmaceuticals and the like against oxidative changes at very low concentrations, without imparting color, odor or precipitates. The antioxidant extract/concentrate according to this invention is a mixture of compounds like sesamol, sesamin, episesamin, sesamolin, related derivatives, tocopherols, polyphenols/ferulic acid, denatured proteins, sugars, lipids, minerals and browning products (maillard reaction products) etc. The process described herein minimises interfering compounds without losing much of the antioxidant lignans, by carefully adopting conditions of the different extraction steps. The antioxidant extract from sesame containing sesamol in higher amounts, prepared by this novel process can be used as a substitute for synthetic antioxidants such as BHA, BHT or TBHQ that are generally used in vegetable oils, foods, cosmetic and pharmaceutical preparations and is non obvious, as the natural antioxidant extract prepared, is soluble/dispersible in oil and oil-water emulsion systems.

The process thus aims at generating basic and applied knowledge. The sesame seed or its cake with antioxidant activity can be utilised as a source for natural antioxidant extract, as a substitute for synthetic antioxidants like BHA, BHT and TBHQ. that are banned due to their demerits in many countries. [(Shahidi, F., Natural Antioxidants—Chemistry, Health Effects and Applications, pp. v, AOCS Press (1997)].

The food that we consume contains mainly biomolecules, which are susceptible to attack, by free radicals. The oxidation of lipids by the free-radical chain reaction viz. lipid peroxidation, is a major concern for both consumers and food manufacturers. In order to prevent these unwelcome changes in lipids and foods, modified atmosphere packaging, vacuum packaging, nitrogen gas substitution etc. are practised. The discovery and use of antioxidants to increase the storage life of foods has made possible the marketing of mainly new products and is of direct economic benefit to consumers. Today antioxidants are widely used in processed foods and also in pharmaceuticals, cosmetics, essential oils and plastics for food packaging. The commonly used antioxidants in foods to control oxidation and prevent off-flavour development include Butylated Hydroxy Anisole(BHA), Butylated Hydroxy Toluene(BHT), Propyl Gallate(PG) and tert-Butyl Hydroquinone (TBHQ) at a maximum permitted usage level of 200 ppm. The widespread use of these synthetic compounds is also backed by development of chemical industries. However, their use in foods has been alerted by many agencies due to safety considerations. The possible toxicity of the synthetic chemicals used as antioxidants has been studied for many years (Johnson and Hewgill, 1961; Branen, 1975) as has been cited in the U.S. Pat. No. 5,043,100 in 1991, by Chang et al. In the same patent cited above, it has been quoted that FDA (Food and Drug Adulteration Act) has expressed concern over the use of BHT as has been reported (Food Chemical News, 1976). The concern stems from scientific literature reviews conducted for the FDA which focused on enzyme inducing effects of BHT on liver and on extraheptic organs, such as lungs and gastrointestinal tract mucosa. As cited in Chang's patent (1991), FDA had expressed concern over the effect of BHT on the conversion of other ingested materials into toxic or carcinogenic substances by the increase of microsomal enzymes. As a result because restrictions have been placed upon the use of such synthetic antioxidants by many European and Asian countries. As cited in the same patent by Chang et al (U.S. Pat. No. 5,043,100 Aug. 27, 1991); BHA has been removed from the GRAS list by the FDA after Nobuyuki Ito of Nagoya City University Medical school in Japan, (1982), reported findings showing BHA to be carcinogenic in rats, BHA is in the process of being carefully scrutinized. TBHQ has not been approved in Japan, Canada and certain European countries. These countries hold that there is insufficient information available on safety of the antioxidant. Moreover, the high cost of synthetic antioxidants in addition to the dubious safety aspects warrants the investigation, preparation and evaluation of natural antioxidants suitable for food and vegetable oil protection. Added to this, there is a tendency for the consumers to reject foods containing synthetic additives and consequently it is a great marketing advantage for the manufacturer to claim a food product as 'all natural'. Efforts have already been started worldwide to find alternates to check lipid oxidation and rancidity development in foods especially naturally occurring components from edible sources. The major dietary antioxidants identified so far are tocopherol, carotenoids, ascorbate etc.

Since an antioxidant is an unavoidable additive, very soon the food, pharmaceutical and cosmetic industries will have no practical options because the only common natural antioxidant viz mixed tocopherols has only weak antioxidant properties. The use of carotenoids is limited due to its high lipid solubility and intense coloration even at low ppm levels of 50-100 ppm. Therefore, the need for safe and effective natural antioxidants is urgent and genuine.

The prior art on natural antioxidants for food uses have patents related to the antioxidants from tea (Chang et al., U.S. Pat. No. 5,043,100, 1991, (United States Patent on Lipid soluble green tea catechin antioxidant solutions, U.S. Pat. No. 5,527,552, 1996 by Todd, Jr. and Paul H.) and from rosemary and other herbs (U.S. Pat. No. 5,753,697 1998 by Joyeux et al. on 'Method and pharmaceutical compositions containing rosmanol derivatives'.), (U.S. Pat. No. 5,017,397, 1991 by Nguyen et al. on 'Process for extracting antioxidants from Labiatae herbs'.). The rosemary extracts at 0.02% level is claimed to show antioxidant activity at least equal to synthetic antioxidant mixture of BHA/BHT(1:1). The disadvantage of these natural antioxidant extracts is that they can not be used at higher concentrations, especially the odoriferous ones, since they impart undesirable flavor taints to foods and other products. In the case of phenolic extracts, the solubility of such antioxidants in vegetable oils is disputable since they are lipophobic. Though they are compounds with confirmed antioxidant activity, extracts containing phenolic/flavonoids may not be suitable for oils and fats due to their poor dispersibility in pure lipids.

At this juncture the protection of foods and oils against oxidation becomes inevitable since free radicals produced during the autoxidation of lipids are injurious. The major recommendation by scientific community to industry is to utilise natural antioxidants available from different sources. At present, Vitamin E, Vitamin C, flavonoids etc are reported as effective natural antioxidants capable of protecting oils from autoxidative changes (N. Nakatani In: *Natural Antioxidants. Chemistry, Health Effects and Applications*. Pp 64-75. Fareidoon Shahidi (Editor), AOCS Press (1997).], [N. Ramaratnam, H. Ochi, and M. Takeuchi. In: *Natural Antioxidants. Chemistry, Health Effects and Applications*, pp 76-95. Fareidoon Shahidi (Editor), AOCS Press(1997)]. However, solubility of the natural antioxidant in oil phase is important if they have to be used with vegetable oils commercially produced. Thus Vitamin C and flavanoids will have to be made miscible in oil phase if they are used with vegetable oils as against aqueous system with oil/water emulsion. This is possible only through modification of their structure through derivatisation by chemical/enzymatic methods. Alternately, effective oil soluble antioxidants and their extracts have to be developed for vegetable oil protection.

Sesame oil which is highly unsaturated (IV 104-109) and commercially extracted by established milling processes is well known for its unusual stability. This is attributable to the antioxidant components and lignans like sesamol (structure 1), Sesamin (structure 2), and sesamolin (structure 3); sesamol is reported to be produced from sesamin during refining/frying steps [Y. H. Hui(Editor)*Bailey's Book on Industrial Oils and Fat Products*. 5th Edn., Vol. 2., Pp 457-495, Wiley International Publication (1996)]. In the present invention, a process for extracting antioxidants from seeds/cake is described and the product, namely the antioxidant extract/concentrate is tested by different methods to ascertain its activity, in protecting crude or refined vegetable oils like soyabean, sunflower, safflower, groundnut oil etc.

Sesamol, the antioxidant compound reported to be present in traces in sesame oil is produced synthetically and added as antioxidant in fat/food products [See K. Kikugawa etal., *J.Amer.Oil Chem.Soc.*, 60, 1528-1533 (1983) as cited in *Bailey's Book on Industrial Oils and Fat Products*. 5th Edn., Vol. 2., Wiley International Publication (1996); Hiromi Yashida etal., *J.Sci.Food Agric.*, 79, 220 (1999)]. Sesamol is reported to be present in sesame oil extracts from sesame in trace quantities only [Y. Fukuda etal., *J.Amer.Oil Chem.Soc.*, 63(8) 1027-1031 (1986)]. In the present invention, sesamol, is extracted in higher quantities in addition to other lignans, by polar solvents such as methanol from sesame seed/cake into an effective antioxidant extract. Sesamol being polar is not extracted into hydrocarbon solvents; it is extracted into oil only in traces in the conventional milling process. Sesamol is not reported by earlier researchers even in aqueous alcoholic extracts of sesame [Yung—Shinshyu and Lucy Sun Hwang, *Food Research International*, 35, 357-365 (2002), Katsuzaki et al. *Phytochemistry*, 35(3), 773-776 (1994), Katzuzaki et al., *Biosci.Biotech.Biochem.*, 56(12) 2087-2088 (1992)]. Hence this is the first report of extraction and quatification of sesamol, the most antioxidant compound in sesame, into an antioxidant extract based on sesame.

Investigations conducted on the unusual stability of sesame oil in spite of its unsaturation has led to the finding that compounds other than tocopherol are naturally protecting the oil from autoxidative changes. Prior investigation by Indian [Satchidanandan Subramanian et al., *J.Nutr.*, 123(11) 1852-1858 (1993)] as well as Japanese workers [Fukuda et al., *J. Amer. Oil Chem. Soc.*, 63(8) 1027-1031(1986)] have shown the presence of compounds like sesamol, sesamolin, sesamin, sesaminol etc. in the analysis of hexane extracts of sesame seed using HPLC; sesamin, sesamolin have been reported in greater quantities and sesaminol and sesamol only in traces. Mimura et al (U.S. Pat. No. 5,132,294; Jul. 21, 1992) have patented the process for preparing antioxidative glycosides and the composition containing the same. In this invention, the applicants have prepared the glycosides from plant cell cultures derived from sesame (*Sesamum indicum* L.) which shows antioxidant activity against linoleic acid oxidation as assayed by the thiocyanate method and with (rabbit) erythrocyte ghost cell methods. Aqueous ethanolic/acetone extracts of sesame seeds have also been reported to contain glycosides of lignans having antioxidant activity. [Katsuzaki et al., *Phytochemistry*, 35(3), 773-776 (1994)]. The glycosides are reported to have antioxidant activity in cell culture studies. The use of glycosides in cosmetic preparations is reported in prior art. However, the glycosides, derived naturally or artificially from sesame, are not dispersible in oil systems for protection and are suitable for emulsions only. Also another US patent has been registered by Kawakishi et al in 1997 (U.S. Pat. No. 5,606,035) in which extracts or compositions from sesame and other added antioxidants such as tocopherols, phenolics etc. also, are claimed to have hypocholestemic effect in animals. This is a patented pharmaceutical formulation.

SUMMARY OF THE INVENTION

Though sesame antioxidants are reported in prior art, there is no disclosure of a process for an antioxidant extract from sesame seed or cake that is an effective substitute for synthetic antioxidants for oil/food protection. Thus the object of this invention is to deliver a natural antioxidant extract from an edible source like sesame seed or sesame cake which is a byproduct of the oil industries, through simple extraction steps. The antioxidant extract according to this invention consists of mainly antioxidant lignan compounds like sesamol, sesamin, episesamin sesamolin, glycosides and related compounds, phenolic acids, denatured proteins, lipids, soluble sugars, minerals etc. The extraction of antioxidants has been tried with different organic solvents of hydrocarbon, alcohol, alkyl ketone and ester types. The separation, idetification and quantification of peaks was carried out by HPLC analysis. The antioxidant activity was evaluated by potassium ferricyanide method [See G. C. Yen and P. D. Duh., *J.Amer.Oil Chem.Soc.*, 70, 353-386 (1993)]., ferric thiocyanate method [See G. C. Yen and C. L. Hsieh., *J.Agric.Food Chem.*, 46, 3952-3957 (1998)] as biochemical methods. The antioxidant efficiency was also tested by evaluating the oxidative stability of refined soybean oil in heated conditions, using Differential Scanning Calorimeter (DSC) and also by invitro stability studies with refined oils by Schaal Oven Test method [Owen R Fennema in: *Principles of Food Science. Part 1. Food Chemistry*, Pp 166-168, Marcel&Dekker Inc. (1976)] which are described subsequently. In the present invention, the natural antioxidant concentrate from an edible source like sesame seed/cake is prepared by organic and or aqueous extractions. The extract(s) so obtained is capable of protecting commonly used vegetable oils, foods etc. against autoxidation and exhibits high level of radical quenching activity as explained later.

Thus, it is an object of this invention that sesame antioxidants can be extracted by alcohols, ketones, esters or substituted hydrocarbon solvents, for 10 hrs to 7 days. The extraction can be carried out over a temperature range of 25-85° C. The extract can be concentrated under reduced pressure by usual laboratory practices and dissolved in a non-ionic, non-aqueous permitted organic solvent or food carrier.

It is also another object of this invention that the starting material can be first treated with hydrocarbon solvents such as pentane, hexane, heptane or mixtures there of, for defatting over a temperature range of 25-85° C. for 10-24 hours, to facilitate subsequent antioxidant extraction.

It is also another object of this invention that the sesame seed/cake is extracted with organic solvents belonging to the group comprising of methanol, ethanol, isopropanol, acetone, dichloromethane, ethyl acetate, etc. over a temperature range of 25 to 85° C. and removal of extraction solvent by usual laboratory practices, under reduced pressure (100-150 mm) leads to an antioxidant extract containing 5.0 to 20.0% of the lignans on dry weight basis of the extract, according to HPLC analysis.

In another object of this invention, the above extract contains sesamol, the important antioxidant compound of sesame, in higher amounts of 10-16% of the total antioxidant compounds of the extract. In addition to sesamol, the extract contains mainly lignan compounds like sesamol, sesamin, episesamin, sesamolin, glycosides and other derivatives including lignan dimers, lipids, soluble sugars, proteins, minerals, browning products etc. and the extract is capable of protecting commonly used vegetable oils like soybean oil, sunflower oil, safflower oil and ground nut oil at concentrations equal to or lower than those of currently used synthetic antioxidants like BHT and TBHQ.

In another object of this invention, the sesame seed/cake (after extraction with hydrocarbon solvents), is optionally washed with water, with or without salts such as sodium chloride at 3-10% (w/v) levels, to remove substances such as carbohydrates and/or proteins interfering with dispersibility/antioxidant activity of the extract.

It is also yet another object of this invention that the starting material, if subjected to above step, is dried below 70° C.

Still another object of this invention is to provide a natural antioxidant extract for protection of vegetable oils, that contains natural component(s) such as sesamol, sesamin, episesamin, sesamolin etc, which are reported to have beneficial biological effects such as hypocholestemic, anti-hypertensive effect, anti-aging effect, anticancer effect etc. [as cited in the review 'The Chemistry and Physiological Functions of Sesame'. Mitsuo Namiki *Food Reviews International,* 11(2), 281-329 (1995)].

Still another object of this invention is to provide an antioxidant extract from an edible/natural source which is also shown to have beneficial health effects like antioxidant/anti-cancer effects.

It is also another object of this invention that the lipids stabilised with sesame extracts according to this invention have positive effects on human health and can be considered as superior to the same lipid stabilised with common synthetic antioxidants.

Still another object of this invention is that the synergy of various lignan and non lignan compounds present in this extract is effective in protection of vegetable oils/foods, at lower concentrations is better than single antioxidants such as sesamol.

It is also yet another object of this invention to provide a natural antioxidant extract that is oil dispersible and does not impart any colour, aroma or flavour when used at lower or moderate (permissible) levels of concentrations.

It is still another object of this invention to provide an antioxidant extract that is efficient in protecting vegetable oils at lower concentrations of 0.005% to 0.02% which is less than that of other natural antioxidants under commercial use and also synthetic antioxidant (0.02%).

It is also another object of this invention that the antioxidant extract when used at 50 to 200 ppm levels contains the actual antioxidant compounds, namely the lignans at 1 to 30 ppm levels only, which is extremely low compared to currently used levels of BHT or TBHQ and other reported natural extracts.

According to another object of this invention, one of the identified starting materials, namely sesame cake, a byproduct of the sesame oil industry currently used mainly as a cattle feed, is value-added by this process resulting in better by-product utilisation.

Accordingly the present invention provides an antioxidant extract from sesame seeds/cakes comprising 5-20% lignan mainly containing sesamol 10-16%; sesamin 60-75%; sesamolin 5-8.8%, tocopherols, polyphenols/ferulic acid, denatured proteins, sugars, lipids, minerals and browning products.

In an embodiment of the invention wherein the extract is capable of protecting commonly vegetable oils at concentration ranging between 5 to 100 ppm.

In another embodiment of the invention the antioxidant extract is effective in protection of vegetable oils/foods at lower concentrations than any other synthetic or natural antioxidant.

In yet another embodiment of the invention wherein the free radical scavenging effect of methanolic extract of sesame cake is about 99% at 1.925 mg/ml concentration of extract.

In still another embodiment of the invention wherein the antiradical power of purified sesame cake extract is $15 \times 10^{-5}$ at $EC_{50}$ of $6.4 \times 10^3$.

Accordingly the present invention provides a process for the extraction of natural antioxidants such as sesamol and lignans from oil seeds and by-products such as sesame seed/cake, the said process comprising defatting of the powdered oil seed or cake with hydrocarbon solvents at 25 to 85° C. at a ratio of 1:1 to 1:7 for 3 to 24 hours, washing the defatted material with water or brine, at a ratio of 1:1-1:5, 3 to 8 times and drying the residue below 70° C. for 6 to 10 hours, and extracting with organic solvents such as alcohols, esters, ketones, over a temperature range of 25-85° C. for 10 hrs to 7 days and concentrating the said extract under reduced pressure of 150-100 mm of Hg and dissolving the said concentrated extract containing 5-20% lignans in a permitted carrier such as pure ethanol/ethylene glycol/propylene glycol, stored under refrigeration till actual use.

According to yet another aspect of this invention the final residue obtained after different steps of extraction(s) of the cake is still high in protein content and may be utilised as cattlefeed or for similar preparations.

The process also uses sesame seeds as the starting material and after the stages of hydrocarbon solvent extraction, oil can be recovered from solvent by usual methods of solvent removal and the final residue can be utilised in the same way as with cake as the starting material.

The antioxidant extract can be used to protect foods, cosmetics, pharmaceuticals etc. also which are currently protected by synthetic antioxidants.

The process can also be carried out with sesame seeds of Red (brown), Black, White and wild varieties (eg. Sesamum malabaricum).

Additional objects and advantages will be apparent from a consideration of the following description and in part will become apparent to those skilled in the art upon examination of the following or may be learned by practice of the invention and may be realized and attained by means of the instrumentalities and combinations particularly pointed out in the appended claims.

BRIEF DESCRIPTION OF THE DRAWINGS

Detailed Legend for Figures

FIG. 1 and FIG. 1a Peroxide Value (milli equivalents of oxygen/Kg.) of Soybean Oil stored at 60° C.
Control: This represents soybean oil without any added antioxidants.
TBHQ 200 ppm: This represents the sample of soybean oil containing the synthetic antioxidant viz. TBHQ at the level of 200 ppm ie. 200 mg per Kg. of the oil.
BHT 200 ppm: This represents the sample of soybean oil containing the synthetic antioxidant BHT at the level of 200 ppm ie. 200 mg per Kg. of oil.
Sesame 5 ppm: This represents the sample of soybean oil containing sesame antioxidant extract at the level of 5 ppm ie. 5 mg per Kg. of oil.
Sesame 10 ppm: This represents the sample of soybean oil containing sesame antioxidant extract at the level of 10 ppm ie. 10 mg per Kg. of oil.
Sesame 50 ppm: This represents the sample of soybean oil containing sesame antioxidant extract at the level of 50 ppm ie. 50 mg per Kg. of oil
Sesame 100 ppm: This represents soybean oil containing sesame antioxidant extract at the level of 100 ppm ie. 100 mg per Kg.

Figure 9:
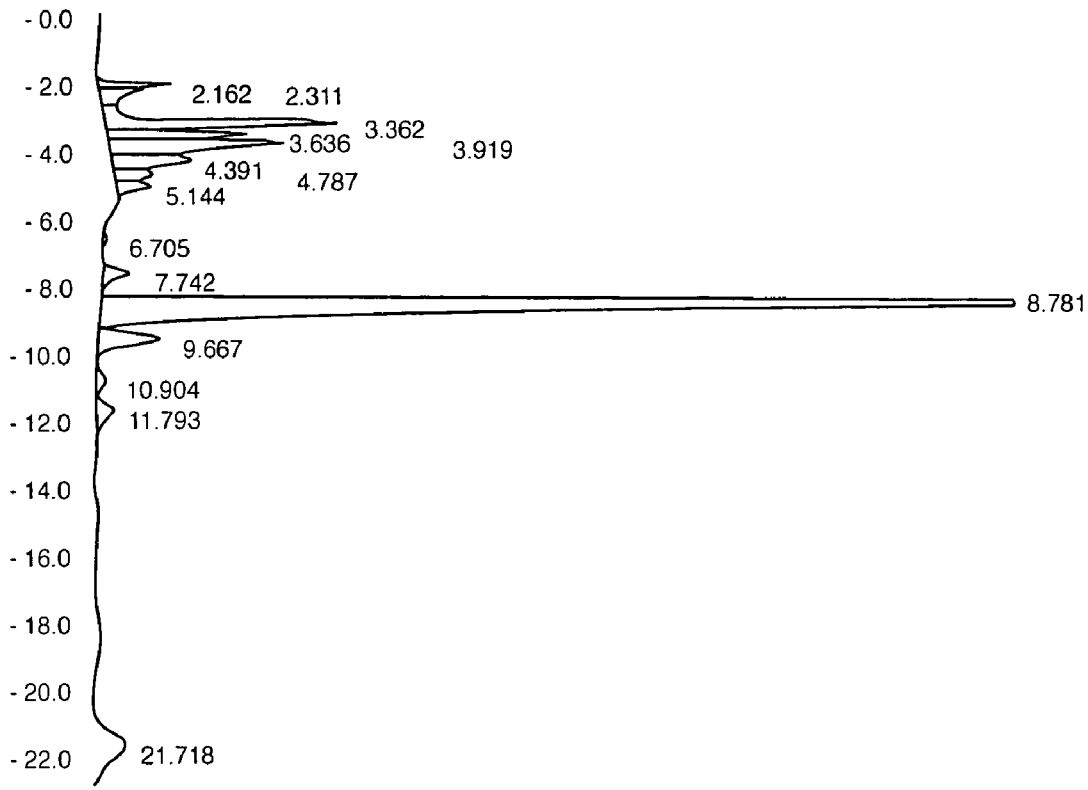

From the plot, it can be seen that sesame extracts, even at low concentrations are more efficient than BHT at maximum permitted levels.

Compare FIG. 1 and FIG. 1a for improved antioxident efficiency of purified sesame cake extract over crude extract.

FIG. 2 Peroxide Value (milli equivalents of oxygen/Kg.) of Safflower Oil stored at 60° C.
Control: This represents safflower oil without any added antioxidants.
TBHQ 200 ppm: This represents the sample of safflower oil containing the synthetic antioxidant viz. TBHQ at the level of 200 ppm ie. 200 mg per Kg.of the oil.
BHT 200 ppm: This represents the sample of safflower oil containing the synthetic antioxidant BHT at the level of 200 ppm ie. 200 mg per Kg. of oil.
Sesame 5 ppm: This represents the sample of safflower oil containing sesame antioxidant extract at the level of 5 ppm ie. 5 mg per Kg. of oil.
Sesame 10 ppm: This represents the sample of safflower oil containing sesame antioxidant extract at the level of 10 ppm ie. 10 mg per Kg. of oil.
Sesame 50 ppm: This represents the sample of safflower oil containing sesame antioxidant extract at the level of 50 ppm ie. 50 mg per Kg. of oil
Sesame 100 ppm: This represents safflower oil containing sesame antioxidant extract at the level of 100 ppm ie. 100 mg per Kg.

From the plot, it could be seen that sesame extracts, at different levels were equally efficient than BHT at maximum permitted levels.

FIG. 3 Peroxide Value (milli equivalents of oxygen/Kg.) of sunflower oil stored at 60° C.
Control: This represents sunflower oil without any added antioxidants.
TBHQ 200 ppm: This represents the sample of sunflower oil containing the synthetic antioxidant viz. TBHQ at the level of 200 ppm ie. 200 mg per Kg. of the oil.
BHT 200 ppm: This represents the sample of sunflower oil containing the synthetic antioxidant BHT at the level of 200 ppm ie. 200 mg per Kg. of oil.
Sesame 5 ppm: This represents the sample of sunflower oil containing sesame antioxidant extract at the level of 5 ppm ie. 5 mg per Kg. of oil.
Sesame 10 ppm: This represents the sample of sunflower oil containing sesame antioxidant extract at the level of 10 ppm ie. 10 mg per Kg. of oil.
Sesame 50 ppm: This represents the sample of sunflower oil containing sesame antioxidant extract at the level of 50 ppm ie. 50 mg per Kg. of oil
Sesame 100 ppm: This represents sunflower oil containing sesame antioxidant extract at the level of 100 ppm ie. 100 mg per Kg.

From the plot, it can be seen that sesame extracts, even at low concentrations are more efficient than BHT at maximum permitted levels.

FIG. 4. Diene Value of Safflower oil stored at 60° C.
Control: This represents safflower oil without any added antioxidants.
TBHQ 200 ppm: This represents the sample of safflower oil containing the synthetic antioxidant viz. TBHQ at the level of 200 ppm ie. 200 mg per Kg.of the oil.
BHT 200 ppm: This represents the sample of safflower oil containing the synthetic antioxidant BHT at the level of 200 ppm ie. 200 mg per Kg. of oil.
Sesame 5 ppm: This represents the sample of safflower oil containing sesame antioxidant extract at the level of 5 ppm ie. 5 mg per Kg. of oil.
Sesame 10 ppm: This represents the sample of safflower oil containing sesame antioxidant extract at the level of 10 ppm ie. 10 mg per Kg. of oil.
Sesame 50 ppm: This represents the sample of safflower oil containing sesame antioxidant extract at the level of 50 ppm ie. 50 mg per Kg. of oil
Sesame 100 ppm: This represents safflower oil containing sesame antioxidant extract at the level of 100 ppm ie. 100 mg per Kg.

From the plot, it could be seen that sesame extracts, at different levels were equally efficient compared to BHT at maximum permitted levels.

FIG. 5. Diene Value of Sunflower oil stored at 60° C.
Control: This represents sunflower oil without any added antioxidants.
TBHQ 200 ppm: This represents the sample of sunflower oil containing the synthetic antioxidant viz. TBHQ at the level of 200 ppm ie. 200 mg TBHQ per Kg.of the oil.
BHT 200 ppm: This represents the sample of sunflower oil containing the synthetic antioxidant BHT at the level of 200 ppm ie. 200 mg BHT per Kg. of oil.
Sesame 5 ppm: This represents the sample of sunflower oil containing sesame antioxidant extract at the level of 5 ppm ie. 5 mg sesame extract per Kg. of oil.
Sesame 10 ppm: This represents the sample of sunflower oil containing sesame antioxidant extract at the level of 10 ppm ie. 10 mg extract per Kg. of oil.
Sesame 50 ppm: This represents the sample of sunflower oil containing sesame antioxidant extract at the level of 50 ppm ie. 50 mg extract per Kg. of oil
Sesame 100 ppm: This represents sunflower oil containing sesame antioxidant extract at the level of 100 ppm ie. 100 mg extract per Kg. of oil.

From the plot, it could be seen that sesame extracts, at lower levels were more efficient compared to BHT at maximum permitted level of 200 ppm.

FIG. 6. DSC profile of oxidative stability of soybean oil containing synthetic and sesame antioxidants at different concentrations. (ppm)

DSC experiments: Differential Scanning Calorimeter. The Mettler Toledo instrument used for carrying out the studies, is configured to follow oxidative stability of vegetable oils at a desired higher temperature under oxygen flow. Vegetable oils were subjected to temperature programmed heating regime under flow of oxygen and it was found that 150° C. was the temperature of inflexion for most of the vegetable oils. Hence, for further studies, isothermal heating of oils at 150° C., under a stream of oxygen at 40 ml per min was selected to evaluate the oxidative stability. With the help of an inbuilt program of the instrument, the induction period in 'time-units' could be calculated. This is indicated in the diagram as 'onset' time. Longer 'onset' time indicates better protection. Crude and Purified extracts were studied. DSC profiles of purified sesame extracts have been included here.

In FIG. 6, the oxidative stability of soybean oil stored at 60° C. for 7 days has been depicted. (The storage study continued for one month. The extent of protection as measured in DSC was studied here.). Each experiment such as Control alone, (soybean oil+BHT), (oil+TBHQ), (oil+Sesame extract at 10 ppm, 50 ppm, 200 ppm) etc were carried out separately. For comparison sake, the different profiles have been overlaid in the same figure. In FIG. 6, the concentrations of BHT and TBHQ are 200 mg per Kg. of oil. For comparison, the profile of oil containing sesame extract at 50 ppm is also depicted in the overlaid diagram. It could be seen that sesame extract at 50 ppm is equally efficient as BHT at 200 ppm.

Explanation of other terms in the Figure.

1. The DSC profile marked as '1' represents soybean oil control sample stored for one(1) week. Onset time 6.27 minutes.

2. The DSC profile marked as '2' represents stored (one week, 60° C.) soybean oil containing BHT at 200 mg per Kg of oil concentration. Onset time 7.30 minutes.

3. The DSC profile marked as '3' represents stored (one week, 60° C.) soybean oil containing TBHQ at 200 mg per Kg. of oil concentration. Onset time 20.48 minutes.

4. The DSC profile marked as '4' represents stored (one week, 60° C.) soybean oil containing sesame antioxidant extract at 50 mg per Kg. of oil concentration. Onset time 7.30 minutes, same as BHT at 200 mg per Kg level.

These results support the data on Peroxide Value estimations and the finding that sesame extract at lower concentration is comparable with BHT at maximum levels, in protecting stored vegetable oils from oxidative changes.

FIG. 7. DSC profiles of safflower oil containing synthetic and sesame extracts at different concentrations.

As explained elsewhere, the Figure represents overlaid DSC profiles of safflower oil containing synthetic and sesame antioxidants at few select concentrations. The onset time has been recorded in the printout of the profile.

FIG. 7 represents DSC profiles of oxidative stability of fresh samples of safflower and sunflower oils.

1. The profile marked as '1' represents control sample of safflower oil. Onset time 4.72 minutes.

2. The profile marked as '2' represents safflower oil containing sesame extract at 50 mg per Kg of oil concentration. Onset time is 5.80 minutes.

3. The profile marked as '3' represents safflower oil containing sesame extract at 100 mg per Kg of oil concentration. Onset time 7.22 minutes.

4. The profile marked as '4' represents safflower oil containing BHT at 200 mg per Kg of oil concentration. Onset time 7.23 minutes.

5. The profile marked as '5' represents safflower oil containing TBHQ at 200 mg. Per Kg of oil concentration. Onset time 10.01 minutes.

Results show that in the case of Safflower oil, sesame extract is effective at lower levels and at 100 mg/Kg level offers protection comparable with BHT at 200 mg/Kg. concentration.

FIG. 8. HPLC Profile of sesame extract

The Indian ink drawing sent along with the patent text as FIG. 8, is the HPLC profile of Sesame cake extract (crude extract of sample). The identified peaks that are confirmed have been marked as 1, 2, 3 etc. Calibration of the peaks have been carried out with standard sesamol which is a known antioxidant constituent, characteristic of sesame and has matching wavelength of maximum absorption of 296 nm ($\lambda_{max}$) and comparable molar absorption coefficient of $\epsilon_{max}$ 29.7 with other compounds identified and marked. Thus, the absorption characteristics of sesamin, and sesamolin as quoted in Bailey's Industrial Oil and Fat Products. (vol.2), V edn. 1996. p 470, are: Sesamin $\lambda_{max}$ 287 and $\epsilon_{max}$ 23.0; Sesamolin $\lambda_{max}$ 288.5 and $\epsilon_{max}$ 21.8.

FIG. 9. HPLC profile of sesame extract is the actual print out from the instrument of the stored data on HPLC profiles One photocopy of the above HPLC profile is also enclosed in which the areas of identified and tentatively identified components (glycosides of sesaminol) have been calculated. The lignan content based on calibrated area of the numbered peaks was 7836 ppm (0.78%) on extract weight basis. On raw material weight basis, the value is 1578.9 ppm.

Figure 10:
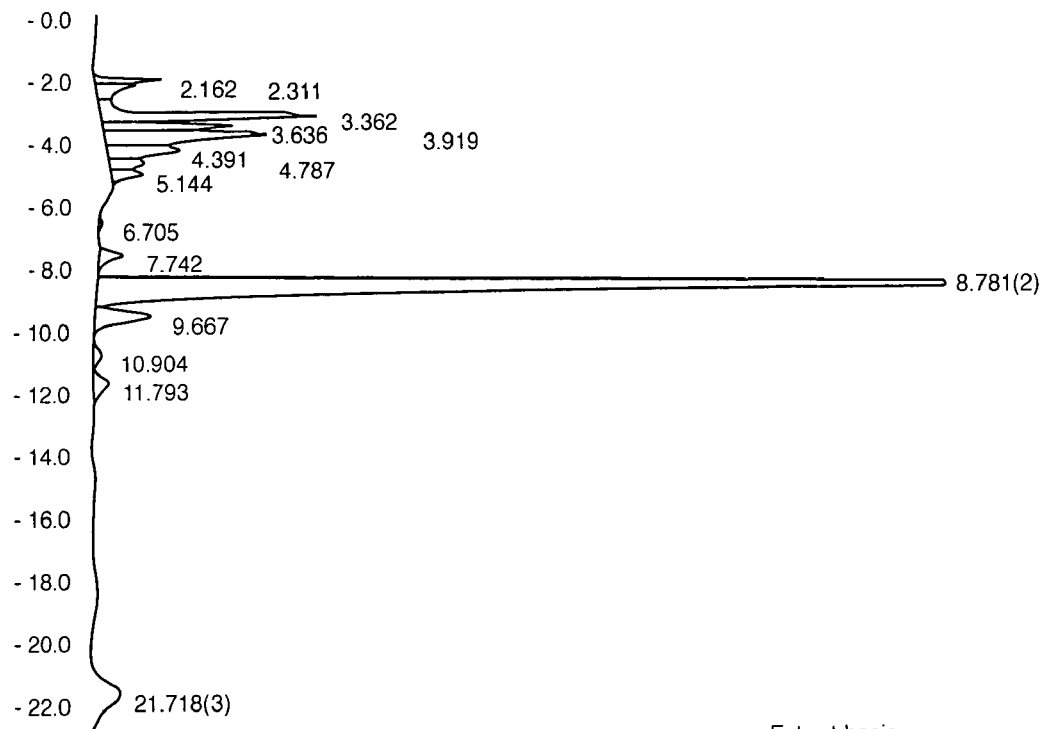

FIG. 10. HPLC profile of sesame extract prepared according to the patentable process, given as FIG. 10 is the actual print out of the stored data from the instrument on HPLC profiles.

One photocopy of the above HPLC profile (FIG. 10) is also enclosed in which the areas of identified and tentatively identified components (eg. glycosides of sesaminol) have been calculated. The lignan content based on calibrated area of the numbered peaks was 1, 40, 914 ppm (14.09%) on extract weight basis. On raw material weight basis, the value is 6887 ppm.

FIG. 11 shows the chemical formulas for Sesamol, Sesamin, and Sesamolin.

DETAILED DESCRIPTION OF THE INVENTION

In order to achieve the foregoing and other objects mentioned and the present invention as embodied and broadly described herein, the process of this invention of extracting antioxidants from sesame seed/cake comprises extracting the starting material with hydrocarbon solvents such as pentane, hexane, heptane or mixtures thereof at 25-85° C. preferably at 25-60° C. at 1:1 to 1:7 ratio for 10-24 hrs, followed by the optional step of washing with water at 1:1 to 1:5 ratio preferably at 1:2 to 1:5 ratio 3 to 5 times or with 3-10% NaCl 1-3 times, followed by water washing 1-4 times and drying below 70° C. under a draft of air including sun drying, followed by extraction with organic solvents such as alcohols/esters/ketones having C1-C5 carbons at a ratio of 1:1-1:7, using usual laboratory extraction procedures such as soxhlet extraction, refluxing, stirring, percolation etc. for 10 hrs to 7 days (when temperatures <30° C. is employed), to extract substantially the antioxidant compounds. The extracts after filtration through a simpler filter aid can be concentrated under reduced pressure at temperatures below 60° C. in a rotary evaporator and the residue can be redissolved in ethanol or any permitted additive carrier such as ethylene glycol, propylene glycol etc.

The extract is concentrated by removing the solvent under reduced pressure towards end and redissolved in pure ethanol or permitted carriers. The residual sesame meal after this final extraction can be reused as cattlefeed, since it is still rich in proteins (37-50%), fibre (8-10%) and minerals (11-15%).

The present invention also relates to a process of producing a natural antioxidant concentrate containing 5 to 20% lignans, as analysed by HPLC.

A typical sample of sesame seed has 40-50% fat content and cake has approximately 6-8% moisture levels are less than 10% in both cases. The starting material is powdered with a steel mortar and pestle or with a similar arrangement and the material is defatted fully or partially with hydrocarbon solvents such as hexane or petroleum ether in the ratio of 1:2 to 1:5 preferably 1:2 to 1:3. The usual laboratory set up like hot extraction by soxhlet, refluxing, cold extraction by stirring etc. are employed.

Accordingly 10 g. to 100 g. samples can be extracted with solvents such as pentane, hexane, heptane or mixtures thereof over a temperature range of 25-85° C. for 10 to 24 hours for defatting. The defatted cake meal can be extracted with alcoholic solvents belonging to a group of solvents comprising of methanol, ethanol, isopropanol etc. or ketones like acetone or esters like ethyl acetate by the usual laboratory procedures of extraction by refluxing, soxhlet, stirring or elution through a column packed with the substance. The extraction time may range from 10 hours to 7 days as mentioned earlier.

The antioxidant efficiency of the extract was evaluated by studying the oxidative stability of commonly used RBD vegetable oils such as soyabean, safflower, ground nut oil.

The oxidative efficiency of the extract was evaluated by studying the oxidative stabilty of commonly used RBD vegetable oils such as soyabean, safflower, sunflower, ground nut oils (without any added synthetic antioxidants) during storage at ambient (28±2° C.) and higher temperatures (60° C.) according to the Schaal Oven Test method. To carry out test, about 15-100 g oil samples were taken in uniform containers, in duplicate with or without headspace and loosely stoppered/covered and incubated at 60° C. In an actual embodiment of the process, the stability studies were conducted using control and experimental samples of the natural antioxidants ranging from 3 to 1000 ppm preferably in the range of 5-200 ppm were used in the experiment. Permitted antioxidants like BHT and TBHQ were also studied over a concentration range of 50-200 ppm. During storage at 60° C., the oil samples were analysed periodically for the peroxide value (AOCS method), Diene value (IUPAC method) and secondary oxidation changes by the anisidine value according to the Jirusova et al., *Nahrung.*, 19, 319 (1975) and fatty acids by GC analysis at regular intervals.

The levels of use of the sesame antioxidant extracts required were much lower (50 to <200 ppm) than the synthetic counterparts which were used at 200 ppm level. The protection offered by sesame extract was comparable/better with that of BHT at 200 ppm level, in both ambient and incubated storage studies. The results are given in FIGS. 1, 2, 3, 4, 5.

The radical quenching efficiency of the extract was also tested by widely reported standard methods like di-phenyl picryl hydrazyl (DPPH) radical according to the methods of W. Brand Williams, M. E. Cuvelier and C. Berset, *Lebesm.-Wiss. U-Technol.*, 28, 25-30 (1995) and the efficiency established as shown in Tables 1&2.

The oxidative stability of vegetable oils containing synthetic antioxidants (BHT and TBHQ at 50-200 ppm) and sesame extract at different levels 3 to 1000 ppm were also tested in the Differential Scanning Calorimeter (Mettler Toledo, model 821) under flow of oxygen (40 ml/min.). The heating regime followed was isothermal at 150° C. and from the curves obtained (FIGS. 6, 7), the 'onset-time' of oxidative changes under identical conditions could be found out by making use of an inbuilt program of the instrument, the induction period represented by the onset time, can be correlated with the onset of rancidity. The experiments showed increased oxidative stability for vegetable oils containing the extract.

The present invention is further described in the following examples which are only illustrative but not limitation for the scope of present invention.

EXAMPLE 1

100 g of the commercial sesame seed was powdered in a steel mortar and pestle and defatted by stirring with 400 ml of hexane in a 5 litre beaker with occasional stirring under ambient conditions (30±2° C.) and covered with petridish for four hours. After four hours, the supernatant layer was decanted off and the residue in the container was stirred with 400 ml of fresh charge of hexane and stirred for 4 hours, with frequent stirring and supernatant solvent layer was decanted off as mentioned above. The extraction procedure was repeated as described above 4 more times. The residue (45 g) was air dried to remove traces of solvent.

EXAMPLE 2

The starting material can be defatted by soxhlet extraction also. In a typical experiment, 100 g of commercially available sesame cake was powdered in a steel mortar and pestle and enclosed in a Whatman 1 filter paper thimble and kept in a soxhlet extractor of 2 litre flask capacity and 700 ml extractor capacity. The soxhlet extraction was continued for 12 hours, in a typical embodiment of the process. The solvent was removed by distillation and traces removed under partial vacuum (<100 mm of Hg.). The residue weighed 92 g in a typical experiment.

EXAMPLE 3

The defatted residue (90 g) of cake was treated with 500 ml of sodium chloride solution of 10% w/v. Soaking time was 1 hour with occasional stirring and decanted. This was repeated at 1:3 ratio two more times. This was followed by washing with water at 1:3 ratio for three (3) times. The residue obtained after these washings was dried below 70° C. in a drier with a draft of air, to get ~63 g.

EXAMPLE 4

The defatted residue (~45 g) obtained from seed was washed with 300 ml of water. Soaking time was 1 hour with occasional stirring and decanted. This was repeated with 200 ml water, 4 times. The residue obtained after these washings was dried below 70° C. in an oven with a draft of air to get ~26 g of meal.

EXAMPLE 5

The residue obtained after defatting and washing as described in examples (2) and (3) was extracted with methanol in a soxhlet extractor. 10 g of the defatted, brine/water washed, residue was extracted in a soxhlet extractor with 200 ml methanol in a soxhlet extractor with 70 ml capacity up to siphoning level of the extractor. The extraction continued for 16 hours. The solvent was removed from the extract by distillation and finally in a rotary evaporator and dried at 60° C. for 2 hours. Cooled in desiccator and weighed. The weight was 1.0 g. About 80% of this extract could be redissolved in 100 ml of ethanol to have a stock solution of the antioxidant.

EXAMPLE 6

HPLC analysis of antioxidant extract by Reverse phase and quantification of separated peaks was performed as follows. In an actual experiment a Shimadzu make LC-10 A D analytical HPLC equipped with a Rheodyne injector with 20 µl sample loop, a UV-Visible detector and C-R7Ae model data analyser was used. The column connected was µ-bondapak column (4.6 mm×25 cm) and solvent system tried was methanol: water (70:30). The UV-detector was set at 290 nm. FIG. 8 represents the HPLC chromatogram. Quantitation of separated peaks was done by calibrating with standard sesamol (Sigma-Aldrich Co., USA). The peaks were identified from coinjection of standards as well as from reports. On HPLC analysis, the extract from Example 5, showed a total lignan content of 55 mg on the extract weight basis. The observed ratio of ingredients namely sesamol, sesamin and sesamolin was 1.0:4.6:0.5.

The range of these compounds in the extracts were sesamol 10-16%; sesamin 60-75%; sesamolin 5-8.8% of the total lignan content of (5-20%) in purified extracts.

TABLE 1

Comparison of free radical scavenging Activity

| Sl. No | Sample | Conc. Of Antioxidant | Free radical Scavenging Effect after 30 min. |
|---|---|---|---|
| 1 | BHT | 20 µM | 81.61 |
| 2 | TBHQ | 20 µM | 98.88 |
| 3 | Catechin | 20 µM | 98.51 |
| 4 | Tannic Acid | 20 µM | 98.88 |
| 5 | Sesame cake extract with MeOH | 1.925 mg/ml | 98.43 |

TABLE 2

Radical quenching activity of antioxidants

| Sample | $EC_{50}$ | Antiradical power* (ARP) |
|---|---|---|
| Sesamol | 75 | $13 \times 10^{-3}$ |
| α-tocopherol | 200 | $5 \times 10^{-3}$ |
| Ascorbic acid | 125 | $8 \times 10^{-3}$ |
| BHT | 300 | $3.3 \times 10^{-3}$ |
| TBHQ | 60 | $16 \times 10^{-3}$ |
| Sesame cake extract | $154 \times 10^3$ | $0.648 \times 10^{-5}$ |
| Sesame cake extract (purified) | $6.4 \times 10^3$ | $15 \times 10^{-5}$ |
| Sesame seed extract | $30 \times 10^3$ | $3.33 \times 10^{-5}$ |

*Antiradical Power(ARP) = $1/EC_{50}$

As a result of the purification steps, the antiradical power improved nearly 24 times as evident from the values of crude and purified extracts respectively.

TABLE 3

Results of crude extraction studies of sesame seed/cake.*

| Sample | Extract weight (%) | Antioxidant lignans in ppm (ie.mg. per Kg.) | | | |
|---|---|---|---|---|---|
| | | Sesamol | Sesamin | Sesamolin | Total |
| 1. Sesame cake extracted with Methanol | 20.2 | 2359 / 477 | 4431 / 895 | 936 / 189 | 8283 / 1561 |
| 2. Sesame cake extracted with Acetone | 20.0 | 590 / 118 | 1661 / 332 | — / — | 2251 / 450 |
| 3. Sesame cake extracted with Ethanol | 14.0 | 569 / 80 | 2608 / 365 | 892 / 125 | 4089 / 570 |
| 4. Sesame cake extracted with Ethyl acetate | 12.4 | 926 / 116 | 5730 / 720 | 2120 / 266 | 8776 / 1102 |
| 5. Sesame cake extracted with Isopropanol | 1.5 | 67.8 | 394 | 22 | 484 |
| 6. Sesame cake extracted with Hexane (ie.cakeoil | 4.9 | — | 3220 / 157 | trace | 3220 / 157 |
| 7. Sesame seed extract with Methanol | 28.5 | 3830 / 488 | 3998 / 510 | 2057 / 262 | 9885 / 1261 |
| 8. Purified extract from cake as per our process | 5.0 | 22676 / 1108 | 1,05738 / 5168 | 12,500 / 611 | 1,40,914 / 6887 |
| 9. Sesame seed extract purified as per our process. | 7.2 | 16733 / 2351 | 3951 / 555 | 2233 / 314 | 22917 / 3220 |

*Conditions of extraction: Soxhlet extraction by respective solvents for 16 hours in taking 10 g sample under same conditions. The extract weight is expressed as % of raw material weight. The antioxidant (lignan) content is expressed as 'parts per million' ie. milligrams of lignans present in 1 kg. of the extract. Alternately, the concentration of lignan as milligrams present in 1 Kg. of the raw material is also calculated and given in blue ink.

The results clearly show that by our process, there is enrichment of antioxidant compounds by 4.5 times at least on raw material weight basis itself.

The main advantages of this invention are:
  The development of a process for the extraction of natural antioxidants from sesame seed/cake effective in protecting vegetable oils, the antioxidant compounds being reported to have beneficial effects.
  The extract is capable of protecting vegetable oils with high unsaturation like soyabean oil at a lower concentration range containing 3 to 30 ppm levels.
  To utilise sesame cake for the extraction of natural antioxidants to be used to protect vegetable oils, thus resulting in value addition to cake.
  After extraction of antioxidants from cake, the cake meal still contains proteins, fibre and sugars and fat to be utilised as cattle feed.

Legend for abbreviations used in the patent text/Figures.

1. ppm: parts per million. Alternately this represents milligram of the chemical/extract per Kilogram of the oil (carrier/matrix).
2. BHT: Butylated Hydroxy Toluene(BHT). Synthetically produced antioxidant permitted in Foods/oils etc. but reported to be deleterious to health and likely to be banned in future. Maximum usage level is 200 ppm ie.(0.02%).
3. TBHQ: tert-Butyl Hydro Quinone. Synthetic antioxidant permitted for use in foods and oils/fats in few countries only. Maximum usage level is 200 ppm (ie. 0.02%).

-continued

| | Legend for abbreviations used in the patent text/Figures. |
|---|---|
| 4. PV: | Peroxide Value, a measure of the oxidative damage of the unsaturated oils. It is expressed as 'milli equivalents of oxygen per Kilogram of oil/fat'. When oils and fats are protected by antioxidants against oxidative changes, the Peroxide Value (PV) of such samples would be lower than the control sample of oil without added antioxidants. |
| 5. AV: | Anisidine Value. This is a measure of secondary oxidation status of oil. Expressed as numerical value only. |
| 6. DV: | Diene Value. This is also a measure of primary oxidation status of the vegetable oil and is expressed as a numerical value only. |
| 7. $EC_{50}$: | Antioxidant concentration needed to decrease the initial [DPPH] concentration by 50%. This value is inversely related to the measure of free radical quenching efficiency of the antioxidant. |

The Applicant reserves the right to claim or disclaim now or in the future any feature, combination of features, or sub-combination of features that is disclosed herein.

All of the numerical and quantitative measurements set forth in this application (including in the description, claims, abstract, drawings, and any appendices) are approximations.

The invention illustratively disclosed or claimed herein suitably may be practiced in the absence of any element which is not specifically disclosed or claimed herein. Thus, the invention may comprise, consist of, or consist essentially of the elements disclosed or claimed herein.

The following claims are entitled to the broadest possible scope consistent with this application. The claims shall not necessarily be limited to the preferred embodiments or to the embodiments shown in the examples.

All U.S. patents, prior-filed patent applications, and any other documents and printed matter cited or referred to in this application are incorporated in their entirety herein by this reference.

We claim:

1. An antioxidant extract from sesame consisting of 5-20% lignan containing sesamol 10-16%; sesamin 60-75%; sesamolin 5-8.8%, and balance being tocopherols, polyphenols/ferulic acid, denatured proteins, sugars, lipids, minerals and browning products.

2. An antioxidant extract as claimed in claim 1 wherein the antioxidant extract is capable of protecting vegetable oils selected from the group consisting of soybean oil, safflower oil, sunflower oil, and groundnut oil at a concentration ranging between 5 to 100 ppm.

3. An antioxidant extract as claimed in claim 1 wherein the antioxidant extract is effective in protection of vegetable oils/foods at lower concentrations than any other synthetic or natural antioxidant.

4. An antioxidant extract as claimed in claim 1 wherein free radical scavenging effect of methanolic extract of sesame is about 99% at 1.925 mg/ml concentration of extract.

5. An antioxidant extract as claimed in claim 1 wherein antiradical power of purified sesame extract is $15 \times 10^5$ at $EC_{50}$ Of $6.4 \times 10^3$.

6. An antioxidant extract from sesame consisting of 5-20% lignan containing sesamol 10-16%; sesamin 60-75%; sesamolin 5-8.8%, and balance being tocopherols, polyphenols/ferulic acid, denatured proteins, sugars, lipids, minerals and browning products, said antioxidant extract made by the method comprising:

defatting of the powdered oil seed or cake with hydrocarbon solvents at 25 to 85 degrees Celsius at a ratio of 1:1 to 1:7 for 3 to 24 hours;

washing the defatted material with water or brine, at a ratio of 1:1-1:5, 3 to 8 times and drying the residue below 70 degrees Celsius for 6 to 10 hours;

extracting with an organic solvent selected from the group consisting of alcohols, esters, ketones, substituted hydrocarbons and combinations thereof, over a temperature range of 25-85 degrees Celsius for 10 hours to 7 days;

concentrating the said extract under reduced pressure of 150-100 mm of Hg;

dissolving the said concentrated extract containing 5-20% lignans in a permitted carrier selected from the group consisting of ethanol, ethylene glycol, propylene glycol and combinations thereof; and storing the dissolved extract under refrigeration until use.

* * * * *